US006313914B1

(12) United States Patent
Roe

(10) Patent No.: US 6,313,914 B1
(45) Date of Patent: Nov. 6, 2001

(54) METHOD AND APPARATUS FOR THE QUANTITATIVE ANALYSIS OF A LIQUID SAMPLE WITH SURFACE ENHANCED SPECTROSCOPY

(75) Inventor: Jeffrey N. Roe, San Ramon, CA (US)

(73) Assignee: Amira Medical, Scotts Valley, CA (US)

( * ) Notice: Subject to any disclaimer, the term of this patent is extended or adjusted under 35 U.S.C. 154(b) by 0 days.

(21) Appl. No.: 09/665,298

(22) Filed: Sep. 20, 2000

Related U.S. Application Data

(63) Continuation of application No. 09/104,749, filed on Jun. 25, 1998, now Pat. No. 6,226,082.

(51) Int. Cl.$^7$ .............................. G01J 3/44; G01N 21/65
(52) U.S. Cl. ............................................. 356/301
(58) Field of Search ............................................. 356/301

(56) References Cited

U.S. PATENT DOCUMENTS

| | | |
|---|---|---|
| 4,169,676 | 10/1979 | Kaiser . |
| 4,427,889 | 1/1984 | Müller . |
| 4,935,346 | 6/1990 | Phillips et al. . |
| 5,079,421 | 1/1992 | Knudson et al. . |
| 5,179,951 | 1/1993 | Knudson . |
| 5,313,941 | 5/1994 | Braig et al. . |
| 5,434,411 | 7/1995 | Miyahara et al. . |
| 5,609,907 | 3/1997 | Natan . |
| 5,610,836 | 3/1997 | Alsmeyer et al. . |
| 5,615,673 | 4/1997 | Berger et al. . |
| 5,864,397 | 1/1999 | Vo-Dinh . |
| 5,866,430 | 2/1999 | Grow . |

FOREIGN PATENT DOCUMENTS

| | | |
|---|---|---|
| WO91/18548 | 12/1991 | (WO) . |
| WO93/09421 | 5/1993 | (WO) . |
| WO95/31930 | 11/1995 | (WO) . |
| WO 98/09153 | 3/1998 | (WO) . |

OTHER PUBLICATIONS

Angel, S.M., et al., "Development of a Drug Assay Using Surface–Enhanced Raman Spectroscopy", SPIE 1990.
Kang, S.Y., et al., "Infrared Absorption Enhancement at Silver Colloidal Particles" *Applied Spectroscopy*, vol. 52, No. 2, 1998, 278–283.
Kellner, R., et al., "Surface–Enhanced Vibrational Spectroscopy: A New Tool in Chemical IR Sensing?", *Applied Spectroscopy*, vol. 52, No. 4, 1997, 495–503.
Kneipp, K, et al., "Single–Molecule Detection of a Cyanine Dye in Silver Colloidal Solution Using Near–Infrared Surface–Enhanced Raman Scattering" *Applied Spectroscopy*, vol. 52, No. 2, 1998, 175–178.
Weldon, M.K., et al., "Surface–Enhanced Raman Spectroscopy of Lipids on Silver Microbes", *Applied Spectroscopy*, vol. 52, No. 2, 1998, 265–269.
Chumanov et al., "Colloidal Metal Films as a Substrate for Surface–Enhanced Spectorscopy", *J. Phys. Chem.*, vol. 99, No. 23, pp. 9466–9471.

Primary Examiner—F. L Evans
(74) Attorney, Agent, or Firm—Burns, Doane, Swecker & Mathis, L.L.P.

(57) ABSTRACT

Surface-enhanced spectroscopy for quantitative analysis of analytes in biological liquid samples. A device for testing a biological liquid sample for the presence or concentration of an analyte includes: (a) a substrate defining a surface which has electrically conductive particles disposed thereon, wherein the surface is adapted to accommodate the liquid sample; (b) means for generating radiation and directing the radiation to be incident on said surface of the substrate so that radiation is emitted from the electrically conductive particles; and (c) means for detecting the emitted radiation. In another embodiment a matrix having electrically conductive particles that are incorporated in the matrix or that are disposed on a surface thereof, wherein the matrix is permeable to the liquid biological sample is used in place of the substrate. The device is particularly suited for determining glucose in human whole blood.

10 Claims, 2 Drawing Sheets

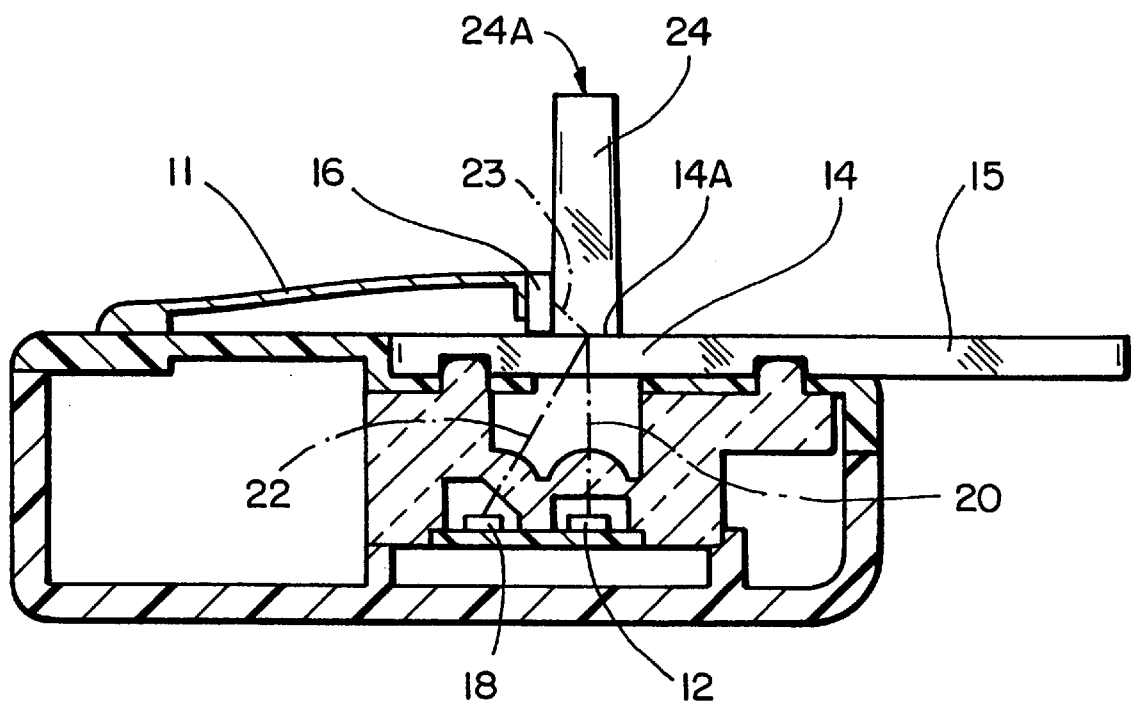
FIG_1A
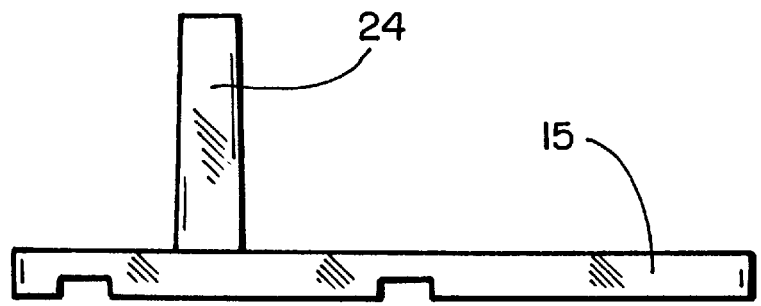
FIG_1B

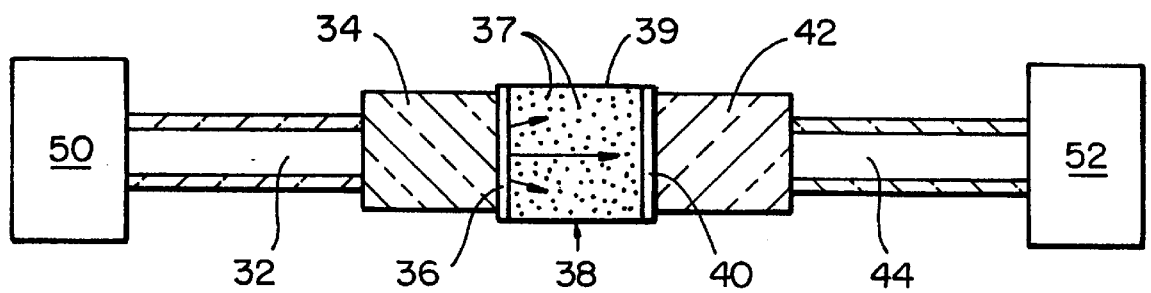
FIG_2
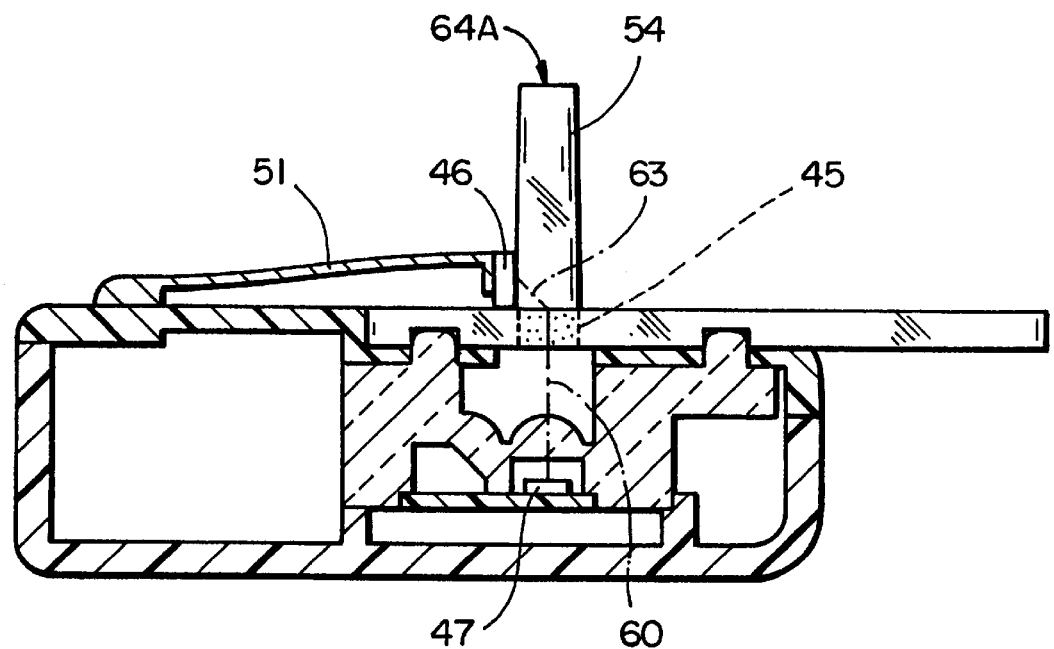
FIG_3

METHOD AND APPARATUS FOR THE QUANTITATIVE ANALYSIS OF A LIQUID SAMPLE WITH SURFACE ENHANCED SPECTROSCOPY

This application is a continuation, of application Ser. No. 09/104,749 filed Jun. 25, 1998 now U.S. Pat. No. 6,226,082.

FIELD OF THE INVENTION

The present invention relates to a device that measures chemical or biochemical components (analyte) in an aqueous fluid, such as whole blood, interstitial fluid or industrial solution. In particular, the invention relates to a test device that includes a substrate incorporating a conductive surface film onto which a drop of aqueous fluid is placed. The presence and/or concentration of an analyte, e.g., glucose, is determined by Raman or infrared spectroscopy whereby radiation is detected from the metallic film, and analyzed for the analyte.

BACKGROUND OF THE INVENTION

Numerous devices have been developed to test for presence and quantity of analytes in aqueous samples, such as whole blood or urine. The patent and technical literature of the last thirty years is replete with inventions which utilize a reagent strip containing a dry chemistry reagent system, that is, a system in which the wet chemistries are imbibed into an absorbent or bibulous medium, dried, and later reconstituted by fluid from the test sample. The reagent strips contain an indicator which changes color, depending on the presence or concentration of a particular analyte in a biological fluid applied to the strip. These strips may be read visually by reference to a color standard or calorimetrically by an instrument calibrated or programmed to detect a certain color. These strips use reduction chemistries, or an oxidizable dye or dye couple. Some of the strips include an enzyme, such as glucose oxidase, which is capable of oxidizing glucose to gluconic acid and hydrogen peroxide. They also contain an oxidizable dye and a substance having peroxidative activity, which is capable of selectively catalyzing oxidation of the oxidizable dye in the presence of hydrogen peroxide. (See, for example, Phillips et al., U.S. Pat. No. 4,935,346.) Examples of these devices have been described to test for glucose, cholesterol, triglycerides, calcium or albumin in whole blood, and for protein, ketones, albumin or glucose in urine.

Dry chemistry reagent strips incorporating enzyme-based compositions are used daily by millions of diabetics to determine blood glucose concentrations. The NIH sponsored study, the Diabetes Complications and Control Trial, demonstrated conclusively that careful control of blood glucose levels can significantly reduce the incidence of serious complications of diabetes such as vision loss and kidney malfunction. Most diabetics must test themselves periodically in order to make appropriate adjustments to their diet or medication. It is thus especially important for diabetics to have rapid, inexpensive, and accurate test strips for glucose determination.

The technologies embodied in the products which have been developed to date have certain limitations from the perspective of the end user and/or the manufacturer. There is, therefore, a need to overcome some of the limitations of currently available testing systems. Specifically, the embodiment of dry chemistry reagent systems in test strips adds sufficient cost to each test strip as to make them too expensive for some diabetics to use on a daily basis. Technology that eliminates the chemistry added to a test strip would reduce cost to the user and allow simpler manufacturing process for production. A direct measurement system would reduce the annual cost of the measurement dramatically by eliminating much of the reoccurring disposable cost.

Infrared (IR) and Raman spectroscopy are analytical methods that provides qualitative and quantitative information on chemical species such as glucose because the presence and intensity of absorption or emission maxima correlate with the presence and concentration of a functional group within the chemical species. A hand held optical instrument that employs these techniques to measure blood glucose directly without chemistry strips would allow inexpensive testing for people with diabetes.

The major restriction of Raman and IR (including NIR) spectroscopy is the high detection limit of the method which results in the techniques not determining low concentrations of trace chemical species such as glucose. For IR spectroscopy, the key to determining the concentration of a trace chemical species is to increase the intensity of the absorption. This can be done by either a pre-concentration technique (evaporation or transfer into a second matrix) or using a long path length through the sample for the IR beam (long path cuvette, multireflection cuvette, multireflection ATR, optical fibers). The pre-concentration step is time consuming and may change the sample. The longer path length requires a large sample size and will also increase the absorbance of the background. For Raman spectroscopy, the key to determining the concentration of a trace chemical species is to increase the intensity of the emission which may also be accomplished with a pre-concentration technique but has the same drawbacks.

Surface-enhanced infrared absorption (SEIR) and Surface-enhanced Raman (SER) techniques can be used to increase the absorption and emission of the chemical species respectively without the drawbacks stated above. This is because it has been shown that chemical species on or near rough metal surfaces achieve a higher absorption or emission of light. Roughened surfaces of colloidal silver, gold, and copper have all been shown to give increased Raman and IR signals in the presence of trace chemical species such as glucose and the process is reversible when the chemical species is taken away. SEIR has been shown to give IR absorption gains of 50 fold and SER has been shown to enhance the ordinary Raman signal by 1.4 million fold. The ability to enhance the glucose signal by these factors because the sample window has a layer of colloidal metal will allow practical detection of solution glucose at physiological concentrations without added chemistry on the test device.

Since the signal enhancement is restricted to the chemical species near the vicinity of the surface, the interface can be selectively monitored without interference from the solution background. There are many different forms of substrate suitable for surface enhancement of IR or Raman signal; these forms include, for example, colloids, electrodes, coated microspheres, fumed silica and acid etched metal surfaces.

Phillips et al., U.S. Pat. No. 4,935,346 describes a system wherein a whole blood sample is applied to the device and indicator development occurs in the presence of the colored components of the sample. Measurements of the color change in indicator are made at two distinct wavelengths to eliminate the interferences from the presence of colored blood components.

Muller, U.S. Pat. No. 4,427,889, describes an apparatus for infrared spectroscopy using two different wavelengths to effect a quantitative measurement in biological medium specifically for the determination of products of metabolism. The level of blood glucose can be determined through absorption analysis of infrared wavelengths absorbed in a glucose containing samples. This approach requires high concentrations of the target component due to the low signal of the technique and the dual wavelength nature of the measurement.

Kaiser, U.S. Pat. No. 4,169,676 describes a method of determining the content of metabolic products in blood using a laser beam that is guided through an attenuated total reflectance (ATR) plate which is placed directly against the skin. Knudson, U.S. Pat. No. 5,079,421; Knudson, U.S. Pat. No. 5,179,951 and Braig, WO 95/31930 describe infrared spectrometric noninvasive methods for measuring the concentration of blood glucose. The methods detect the absorption of infrared radiation by glucose in human tissues.

Braig, U.S. Pat. No. 5,313,941; Clift, WO 91/18548 and Clift, WO 93/09421 describe techniques of applying infrared radiation having multiple wavelengths to measure glucose in blood without interference from overlapping components. Short bursts or pulses of radiation are employed to prevent burning of the tissue.

Berger et al., U.S. Pat. No. 5,615,673, describes an apparatus for measuring analytes in blood and tissue using Raman spectroscopy. The method is suitable for in vitro and in vivo transdermal blood analysis.

Alsmeyer et al., U.S. Pat. No. 5,610,836, describes a method of applying radiation having multiple wavelengths to a sample containing an unknown constituent. Analysis of a sample of unknown constitution often produces data that are perturbed by conditions prevailing at the data collection site. By analyzing multiple variables in a matrix format, a calibration function to determine constituent concentration can be obtained that adjusts for operational variability associated with the measuring apparatus and other changes in the measurement volume.

Despite the advances in conventional devices and methods, the art is still in search of improved techniques for analysis of biological fluid samples, and especially for analysis of glucose in blood. In particular, there is a need for a portable, inexpensive, and easy to use device for glucose detection that does not require chemical reagents.

SUMMARY OF THE INVENTION

The present invention is based in part on the recognition that surface-enhanced spectroscopy is particularly suited for quantitative analysis of analytes in biological liquid samples.

Accordingly, in one aspect, the invention is directed to a device for testing a biological liquid sample for the presence or concentration of an analyte that includes:

(a) a substrate defining a surface which has electrically conductive particles disposed thereon, wherein the surface is adapted to accommodate the liquid sample;

(b) means for generating radiation and directing the radiation to be incident on said surface of the substrate so that radiation is emitted from the electrically conductive particles; and (c) means for detecting the emitted radiation.

In another aspect, the invention is directed to a device for testing a liquid biological sample for the presence or concentration of an analyte that includes:

(a) a matrix having electrically conductive particles that are incorporated in the matrix or that are disposed on a surface thereof, wherein the matrix is permeable to the liquid biological sample;

(b) means for generating radiation and directing the radiation to be incident on matrix so that radiation is emitted from the electrically conductive particles; and (c) means for detecting radiation that is emitted from the metal particles.

By means of the method of this invention it is possible, for instance, to determine glucose in human whole blood rapidly and dependably. It is also possible to measure other blood components such as ethyl alcohol, urea, uric acid, lipids, hemoglobin, creatininie and peptide decomposition products.

In a preferred embodiment the device includes a transparent window that is coated with silver colloid on a sample application side. Blood can be applied to the window in the form of a drop, smear or film and the glucose concentration determined after multispectral analysis from the side opposite the silver colloid. The reading or measuring for the presence/concentration of the glucose is accomplished by detecting the change in reflectance of multiple wavelengths from the colloid layer. The test device can be wiped or washed after blood application for repeat blood application and measurement if desired. If the test device window is scratched or damaged it can be replaced, otherwise the entire system is reusable. No reoccurring disposable cost is incuned for multiple readings.

The devices of the present invention are simpler to use and are less expensive to manufacture relative to most devices previously available. This is especially important for diabetics who rely on blood glucose testing multiple times per day to keep their disease under control.

BRIEF DESCRIPTION OF THE DRAWINGS

FIGS. 1A and 1B are cross-sectional views of a device for analyzing body fluids wherein the device includes a transparent substrate layer;

FIG. 2 is a cross-sectional view of a device for analyzing body fluids wherein the device includes a fiber optic interface; and FIG. 3 is a cross-sectional view of a device for analyzing body fluids which includes a matrix having electrically conductive particles incorporated therein.

DETAILED DESCRIPTION OF THE INVENTION

The invention is directed to methods and devices that employ surface-enhanced infrared absorption or Raman-scattering to measure analytes in liquid biological samples. While the invention will be described with respect to detecting glucose in human whole blood, it is understood that the invention is applicable to measure other blood components such as, for example, cholesterol, high density lipoprotein, low density lipoprotein, ethyl alcohol, urea, uric acid, lipids, hemoglobin, hemoglobin A1C, creatinine and peptide decomposition products. In addition, it is understood that the other biological fluids including, for example, interstitial fluids and urine can be analyzed.

FIG. 1A shows an embodiment of a device for detecting the presence of analytes in a biological fluid sample using surface-enhanced spectroscopy. The device comprises a substrate support 14 made of a transparent material which means that the material will transmit radiation at least at the measuring wavelength(s) employed. The substrate surface 14A contains electrically conductive particles. These particles provide surfaces to which analytes become associated thereby creating the environment for surface-enhanced spectroscopy. By "associated" is meant that the analyte can be, for example, located adjacent to the particles and/or can be chemisorbed thereon to induce surface enhanced spectroscopy. These particles can be present in any convenient form. For example, they can comprise individual islands on the substrate that are formed by evaporation. Alternatively, they can be present as colloidal particles in a transparent film that is cast onto the substrate. A preferred method of creating the particles is to fabricate a rough metal film on the surface of the substrate. By "rough metal film" is meant that the film includes metal particles on the surface onto which analyte can becomes associated. Situated and below substrate 14 is radiation source 12 which directs radiation 20 toward the substrate and situated on one side is radiation detector 18 which detects radiation 22 from the substrate.

To facilitate placement of the blood onto the surface, the substrate is attached to hollow receiving member 24 which is removable from the radiation source 12 and radiation detector 18 as shown in FIG. 1B. In use, one or more drops of blood are placed in the substrate surface through opening 24A of the receiving member. Thereafter, the receiving member is placed in position as shown in FIG. 1A using handle 15. The receiving member is held in place with flexible clamp 11.

For surface-enhanced Raman spectroscopy, the radiation source is selected to generate radiation having a wavelength that causes appreciable Raman-scattering in the presence of the analyte being measured. Although it is known that Raman-scattering occurs essentially at all wavelengths, typically, the radiation employed will be near infrared radiation since ultra-violet radiation often causes fluorescence. When the analyte being detected is glucose, the wavelength preferably ranges from about 300 nm to about 1000 nm. The scattered beam 22 is detected by detector 18.

In an alternate embodiment, the device includes radiation detector 16 which is positioned above substrate 14. Detector 16 is positioned at the end of reflexible clamp 11. The radiation detector detects scattered beam 23 which is emitted from the surface. It is necessary that receiving member 24 be fabricated of transparent material or that it has a transparent window 28 through which scattered beam 23 can travel.

The device of FIG. 1A can also be employed for surface-enhanced infrared absorption spectroscopy. In this case, the radiation source generates an infrared radiation having a wavelength that causes infrared absorption in the presence of the analyte. Typically, infrared radiation having a wavelength that ranges from about 1 $\mu$m to about 15 $\mu$m is employed. Where the analyte being detected is glucose, the wavelength preferably ranges from about 6 $\mu$m to about 11 $\mu$m.

The surface area of substrate 14 is sufficient to accommodate a drop of biological sample, e.g., blood, which typically comprises about 1 $\mu$l to 10 $\mu$l in volume. The substrate typically is constructed of a transparent material such as, for example, acrylic, polycarbonate, styrene, quartz, ZnSe and germanium. The transparent substrate is so selected that it has only slight absorption in the wavelength region(s) of interest for the measurement. The transparent substrate can be constructed as a flat device such as a microscope slide. Alternatively, the substrate can define a trough, flow through, or well with a known volume.

When a rough metal film is employed it can be fabricated on the surface of the substrate by conventional means including, for example, magnetron sputtering and electron-beam evaporation. The metal typically comprises gold, silver, platinum, copper or alloys thereof. The film will typically have a nominal thickness of about 0.1 $\mu$m to 10 $\mu$m and preferably about 0.1 $\mu$m to 1 $\mu$m. The electrically conductive particles material are preferably made of gold, silver, platinum, copper, and alloys thereof, or they are carbon particles or they are coated microspheres that comprise silica particles that are coated with an electrically conductive material. The electrically conductive material particles typically range from about 10 nm to 10,000 nm and preferably from about 30 nm to 100 nm in size.

The device of FIG. 1A can employ conventional sources of radiation such as, for example, light emitting diodes, laser diodes, and tungsten halogen lamps, and conventional radiation detectors such as, for example, silicon, lead sulfide, InGaAs detectors for Raman-scattering and InSb and PbSe detectors for infrared absorption.

FIG. 2 shows another embodiment of the present invention which employs a transparent matrix 38 having electrically conductive materials affiliated therewith to produce surface-enhanced spectroscopy. The matrix is positioned to receive radiation from radiation source 50 through excitation fiber 32, lens 34, and filter 36. Radiation from the matrix is collected by detector 52 through filter 40, lens 42, and collection fiber 44. The same sources of radiation and detectors as described for surface-enhanced Raman scattering and infrared absorption can be employed.

FIG. 3 shows an embodiment of a device, which is similar to the one of

FIG. 1A, that employs a transparent matrix having electrically conductive materials affiliated therewith. The device includes radiation source 42 and radiation detector 46 which is positioned in clamp 51. The device is designed to accommodate a detachable hollow receiving member 54 that includes matrix 45 with electrically conductive materials incorporated therein. In use, after blood is placed in the matrix through opening 64A of the receiving member it is positioned and held in place with flexible clamp 51 as shown. Radiation beam 60 is directed toward the matrix and reflected radiation 63 is detected by detector 46.

The term "matrix" refers to transparent material with sufficient structural integrity to support conductive particles either along a matrix surface and/or incorporated in the core of the matrix. As shown in FIG. 2, in this embodiment, the matrix has electrically conductive particles 37 embedded in the matrix and has electrically conductive particles on surface 39. These electrically conductive particles can be formed in the same manner as the electrically conductive particles employed in the device of FIG. 1. The matrix must be capable of absorbing the liquid biological sample so that the analyte will become associated with the surface of the electrically conductive particles. Preferred matrices include, for example, porous membranes which are polymeric materials, and gels which are colloids in which the disperse phase has combined with the continuous phase to produce a viscous jelly-like product.

A method of preparing a suitable porous membrane having electrically conductive particles distributed throughout the membrane entails immersing a polymer membrane into a mixture containing electrically conductive particles and solvent, and thereafter removing the solvent. Preferred polymers include, for example, polyamides (e.g., NYLON), polysulfone, polystyrene, cellulose acetate and nitrocellulose. Another method of preparing the porous membrane containing conductive particles is to form a mixture containing monomers and/or partially polymerized polymers, conductive particles, and solvent and thereafter causing polymerization.

Suitable gels can be prepared by forming a mixture containing a suitable polymer, electrically conductive particles and solvent thereafter removing the solvent. Suitable polymers include, for example, polyhema, hydrogels, ethylmethylacrylate and polyhydroxy gelatin.

Devices of the invention preferably employ optical sources that produce radiation having multiple wavelengths and one or more detectors for reading the reflected signals. The detectors can incorporate filters or beam splitters to separate the different wavelength components in the radiation. Alternatively, the optical sources can comprise multiple radiation sources each producing radiation of a single wavelength and the radiation sources are activated sequentially. For any particular analyte, selection of specific multiple wavelength radiation where desired can be accomplished by standard mathematical techniques such as chemometric or statistical analysis.

Glucose has viable absorption peaks in a broad region from 1 $\mu$m–12 $\mu$m. The major absorbances are multiple peaks centered around 1.6 $\mu$m, 2.1 $\mu$m, and 9.3 $\mu$m with 9.68 $\mu$m being the strongest glucose absorption peak in this broad region. Because blood is a multi-component solution, multiple wavelengths are employed at not only the absorbance peaks of glucose, but also at the absorbance peaks of chemical species that overlap or interfere the absorption signature of glucose.

The devices preferably include an optic system with lenses to focus the light emitted onto the test area and to focus the reflected light onto a detector. This conserves energy and minimizes the amount of light required by the device to make the measurement.

When the liquid test sample is applied, a thin layer of the target analyte, e.g., glucose, covers the total surface. The penetration depth of the emitted light is larger than the thickness of the metal island film with target analyte absorbed. The amount of reflected light from the film will vary depending on the amount of target analyte in the test sample. The light will be detected with the appropriate detector and the signal analyzed to determine analyte concentration.

The optics modules are calibrated during the manufacture of the test device. In the preferred embodiment, calibration is based on the response produced by a specific set of calibration fluids. By doing this, there is no need to presort and test the LEDs, significantly reducing the cost of the optics module. In addition, this calibration step during manufacture allows the device to compensate for a wide area of variables normally found in reflectance systems. The specific calibration data for the test chips shipped with the test device are stored in the units read only memory.

A more traditional approach to calibration may alternatively be taken. A calibration algorithm, with several settings if necessary, could be programmed into the system if the test device has a longer projected life.

With the present device no prism or total internal reflection plane is required.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. A device for testing a biological liquid sample for the presence or concentration of glucose comprising:
   (a) a substrate defining a surface which has a material disposed thereon which material said glucose will become associated therewith, wherein the material consist essentially of electrically conductive particles and wherein the surface is adapted to accommodate the liquid sample;
   (b) means for generating radiation and directing the radiation to be incident on said surface of the substrate so that radiation is emitted from the electrically conductive particles wherein the radiation generation means comprises:
      (i) a radiation emitting laser;
      (ii) a fiber optic device having an input end that is coupled to the laser for delivering the radiation to irradiate a region of the substrate having a biological liquid sample thereon; and
      (iii) a first optical filter having an input end that is coupled to a distal end of the fiber optic device that filters radiation and an output end for passing the laser radiation; and
   (c) means for detecting the emitted radiation which measures Raman scattered radiation.

2. The device of claim 1 wherein the substrate is transparent to radiation directed to be incident on the substrate surface.

3. The device of claim 1 wherein the radiation generated has a wavelength that ranges from about 300 nm to 1000 nm.

4. The device of claim 1 further comprising means to generate a spectral representation from the detected radiation.

5. The device of claim 1 wherein the substrate comprises a metal film having metal particles on a surface of the film.

6. The device of claim 5 wherein the metal film comprises a metal that is selected from the group consisting of gold, silver, platinum, copper, and mixtures thereof.

7. The device of claim 6 wherein the metal film has a nominal thickness that ranges from about 0.1 $\mu$m to 10 $\mu$m.

8. The device of claim 1 wherein the electrically conductive particles are selected from electrically conductive carbon and metal coated microspheres.

9. The device of claim 1 wherein the electrically conductive particles are disposed on the substrate by sputtering or evaporation.

10. The device of claim 8 wherein the electrically conductive particles are disposed on the substrate by sputtering or evaporation.

* * * * *